US008187235B2

(12) United States Patent
Kataoka

(10) Patent No.: US 8,187,235 B2
(45) Date of Patent: May 29, 2012

(54) PROTECTOR AND PROTECTOR ASSEMBLY

(75) Inventor: Ryoji Kataoka, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 60 days.

(21) Appl. No.: 12/671,630

(22) PCT Filed: Jul. 2, 2008

(86) PCT No.: PCT/JP2008/061948
§ 371 (c)(1),
(2), (4) Date: Feb. 1, 2010

(87) PCT Pub. No.: WO2009/016908
PCT Pub. Date: Feb. 5, 2009

(65) Prior Publication Data
US 2011/0166533 A1 Jul. 7, 2011

(30) Foreign Application Priority Data
Aug. 2, 2007 (JP) ................................. 2007-201496

(51) Int. Cl.
*A61M 5/00* (2006.01)
(52) U.S. Cl. ......................................................... 604/263
(58) Field of Classification Search .................. 604/192, 604/198, 164.08, 263
See application file for complete search history.

(56) References Cited

U.S. PATENT DOCUMENTS

| 4,232,669 | A | | 11/1980 | Nitshke | |
|---|---|---|---|---|---|
| 4,747,836 | A | | 5/1988 | Luther | |
| 4,872,552 | A | * | 10/1989 | Unger | ........................... 206/365 |
| 5,312,359 | A | * | 5/1994 | Wallace | .................... 604/164.08 |
| 5,632,732 | A | * | 5/1997 | Szabo et al. | ................... 604/192 |
| 6,436,086 | B1 | | 8/2002 | Newby et al. | |
| 6,695,819 | B2 | * | 2/2004 | Kobayashi | ..................... 604/192 |
| 2002/0141904 | A1 | | 10/2002 | Rosen et al. | |

FOREIGN PATENT DOCUMENTS

JP 2000-140110 A 5/2000

OTHER PUBLICATIONS

International Search Report (PCT/ISA/210) issued on Oct. 7, 2008 by Japanese Patent Office as the International Searching Authority for International Application No. PCT/JP2008/061948.
Written Opinion (PCT/ISA/237) issued on Oct. 14, 2008 by Japanese Patent Office as the International Searching Authority for International Application No. PCT/JP2008/063387.

* cited by examiner

*Primary Examiner* — Jackie Ho
*Assistant Examiner* — Michael J Anderson
(74) *Attorney, Agent, or Firm* — Buchanan Ingersoll & Rooney PC

(57) ABSTRACT

A protector includes a supporting member mounted on a needle assembly having a needle main body; an outer cover member arranged to incline to the needle main body by having an arm axially supported to the supporting member; and an inner cover member arranged inside the outer cover member. The outer cover member has a cylindrical body having a needle slit extending in an axial direction for insertion of the needle main body. The inner cover member has an arcuate column, which interlocks with the needle assembly when the outer cover member inclines to insert the needle main body into the needle slit, and rotates by sliding on the inner surface of the cylindrical body. The arcuate column has a circular arc cross-section with an area facing at least the needle slit opened to the cylindrical body at an opened position, the needle slit being covered at a closed position.

11 Claims, 15 Drawing Sheets

PROTECTOR AND PROTECTOR ASSEMBLY

TECHNICAL FIELD

This invention relates to a protector and a protector assembly for covering a needle for medical applications used in blood collection, blood transfusion, infusion and so forth.

BACKGROUND ART

For blood collection, blood transfusion, and infusion, a needle for medical applications is known, which is connected to and used together with a blood collecting device, a blood transfusion set, an infusion set, or the like for a blood bag, or a blood processing circuit (such as a blood component collection circuit or a hemodialysis circuit). The needle after having been used is preferably covered with such a protector, as disclosed, for example, in Japanese Laid-Open Patent Publication No. 2000-140110 (U.S. Pat. No. 6,436,086 B1, U.S. Patent Application Publication No. 2002/0141904 A1), in order to prevent the needle from being touched inadvertently. In accordance with such a protector as just described, it is possible to tilt a shield in order to cover the needle, whereby the needle, after use thereof, can be prevented from being touched inadvertently.

Incidentally, in the protector disclosed in Japanese Laid-Open Patent Publication No. 2000-140110 mentioned above, three sides of the needle can be covered. However, the remaining one side face of the needle is left almost open, and there is the possibility for blood that sticks to the needle to possibly leak out from the opening.

DISCLOSURE OF THE INVENTION

An object of the present invention is to provide a protector and a protector assembly, which can cover a needle before and/or after use thereof through a simple procedure.

According to the present invention, a protector, which includes a supporting member mounted on a needle body, and a protector main body, which includes an outer cover member tiltably provided with respect to the supporting member, and an inner cover member provided on an inner side of the outer cover member, is characterized in that the outer cover member has a cylindrical body on which a needle slit is provided, through which a needle of the needle body passes and which covers the needle. Further, the inner cover member has a shield plate, which is capable of moving along an inner face of the cylindrical body, between an opening position at which the needle slit is opened and a closing position at which the needle slit is closed.

In this manner, if the outer cover member is tilted in a direction toward the needle, then the needle is admitted into the outer cover member through the needle slit, and the shield plate of the inner cover member is rotated in an interlocking relationship and covers the needle slit after the needle has passed through the needle slit. Consequently, the needle after use thereof cannot be touched in error. Further, the needle remains covered over the entire circumference thereof by the outer cover and the inner cover, so that leakage of blood can be prevented.

Further, the invention may be configured such that, when the needle is covered by the protector main body, the shield plate moves from the opening position to the closing position in an interlocking relationship with movement of the needle body, when the needle is inserted into the needle slit to close the needle slit.

The invention may be configured such that the outer cover member includes an outer bottom for closing a proximal end side of the cylindrical body, and a cutaway portion, which is provided on the outer bottom and into which the needle body can be inserted. Further, the inner cover member may have an inner wall provided on the proximal end side of the shield plate, wherein the inner wall has a needle receiving edge portion with which the needle body is contacted when the needle body is inserted into the cutaway portion, and a detachment preventing end portion for preventing detachment of the needle body.

The invention may also be configured such that the needle receiving edge portion is provided at a position displaced in a direction perpendicular to the direction in which the needle main body passes, with reference to a center axis of the inner cover member at the opening position, and crosses with the cutaway portion. Further, the detachment preventing end portion may be configured so as to close the cutaway portion when the detachment preventing end portion is at the closing position.

With the configurations described above, if the needle body is brought into contact with the needle receiving edge portion of the inner bottom, then a torque is generated that pushes the needle receiving edge portion down, whereby the shield plate can be pivoted. Further, when the shield plate arrives at the closing position, the detachment preventing end portion can prevent detachment of the needle body. The detachment preventing end portion may have any shape that is capable of preventing detachment of the needle body. The detachment preventing end portion may have, for example, a curved shape, a bent shape, or the like.

The invention may be configured such that the cylindrical body includes a circumferential slit that extends in a circumferential direction, the inner cover member includes a projection for engaging with the circumferential slit, and the shield plate is configured so as to be movable from the closing position to the opening position while the projection moves along the circumferential slit. The circumferential slit need not be formed strictly in a circumferential direction. Since the shield plate engages with the circumferential slit of the tubular member, the shield plate is guided in the circumferential direction, and the shield plate does not come off from the tubular member upon rotation thereof.

The needle slit and the circumferential slit may communicate with each other, and the shield plate may move the projection in an axial direction along the needle slit. As a result of this configuration, upon assembly, the shield plate is inserted into the tubular member with the projection adjusted toward the needle slit, and after the projection reaches the position of the circumferential slit, the shield plate is rotated in the circumferential direction. Further, the outer cover member and the inner cover member can be produced as separate members, so that assembly thereof can be facilitated.

The invention may be configured such that the cylindrical body has a conical shape whose diameter increases toward a distal end side thereof, such that when the shield plate is moved from the closing position to the initial end position, the needle body is positioned inside of the outer cover member.

The invention may be configured such that the cylindrical body comprises a circular cylinder having a substantially fixed diameter, such that a center axis of the outer cover member is provided at a position displaced in a direction in which the needle passes, with reference to a center axis of the inner cover member.

When the tubular member and the shield plate are defined by a circular cylinder and an arcuate cylinder, respectively, the configuration is compact. When the center axis of the outer cover member is displaced in a direction in which the needle passes with respect to the inner cover member, the distance over which the needle body moves can be assured, and reliable operation can be anticipated.

If at least one of the outer cover member and the inner cover member includes a lid member for closing the distal end thereof, then leakage of blood from the needle can be prevented with a higher degree of certainty.

According to the present invention, a protector assembly is characterized in that the protector assembly includes the protector described above, and the needle body on which the supporting member of the protector is mounted.

The needle receiving edge portion may be provided at a position displaced in a direction perpendicular to the direction in which the needle passes, with reference to a center axis of the inner cover member at the opening position.

When the distance between the center of the needle slit and a center axis of the inner cover member is equal to or greater than one half the radius of the needle body, but equal to or smaller than twice the radius of the needle body, the needle body can apply torque sufficiently to the inner cover member, and the protector can be reduced in size.

The above objects, features and advantages of the present invention will become more apparent from the following descriptions of preferred embodiments when taken in conjunction with the accompanying drawings.

BEST MODE FOR CARRYING OUT THE INVENTION

Below, a protector and a protector assembly according to the present invention shall be described in connection with a first embodiment and a second embodiment of the present invention, with reference to FIGS. 1 through 15 of the accompanying drawings.

Figure 1:
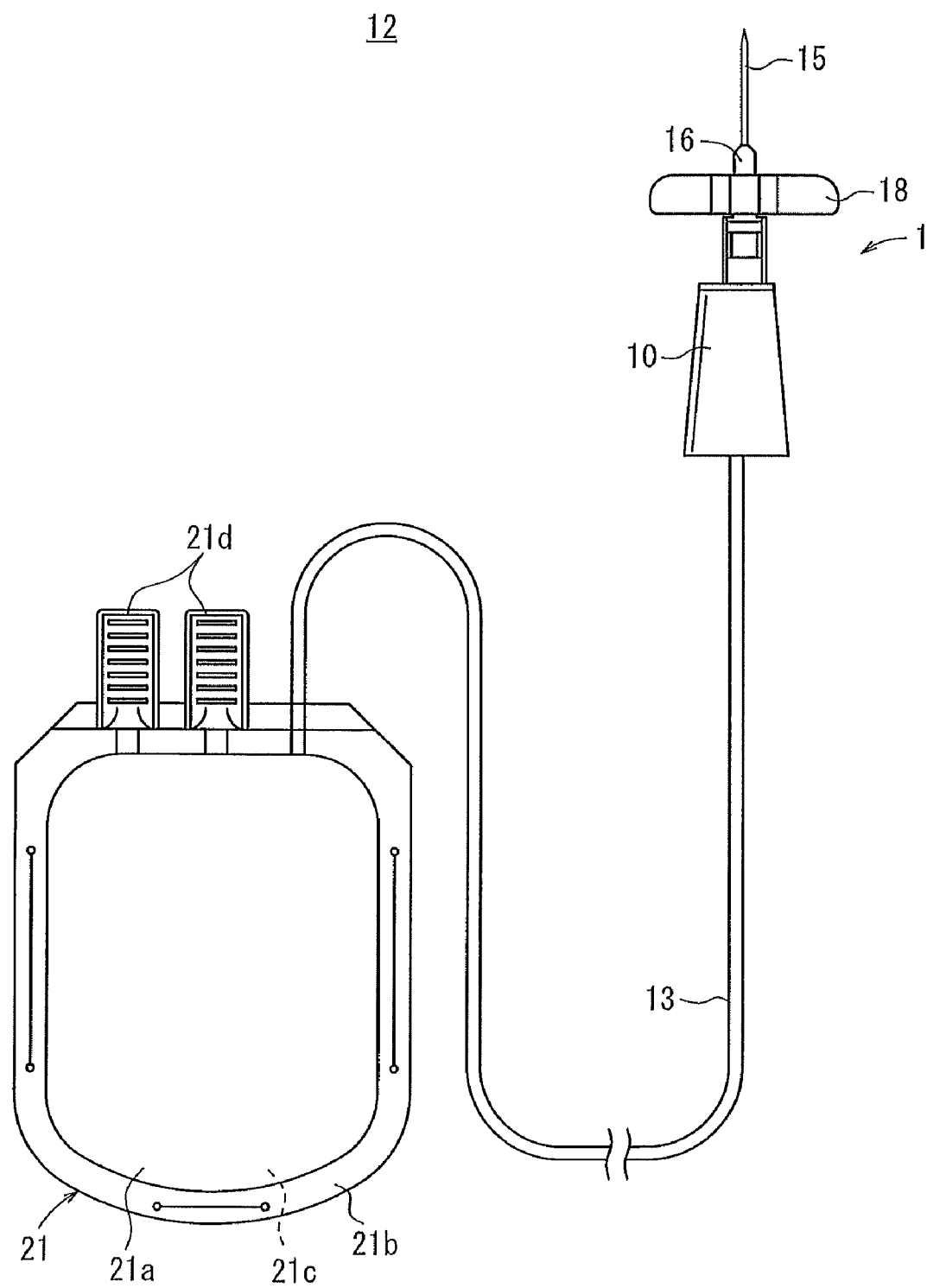
FIG. 1 is a schematic view of a blood bag.

As shown in FIG. 1, the protector 1 according to the first embodiment has a protector main body 10, and a supporting member 18 for holding the protector main body 10 while enabling tilting movement thereof. The supporting member 18 is mounted on a needle assembly (needle body) 14 of a blood bag (blood collecting device) 12. A protector assembly is formed from the protector 1 and the needle assembly 14. The blood bag 12 includes a tube 13, the needle assembly (needle body) 14 connected to an end of the tube 13, and a blood collection bag 21 connected to the other end of the tube 13. Soft polyvinyl chloride, polyolefin, and so forth can be used as materials for the tube 13.

The blood collection bag 21 is formed by placing sheet materials 21a, which are made of a soft and flexible resin such as, for example, polyvinyl chloride, one on the other and fusion bonding (heat sealing, high-frequency welding) or adhering the sheet materials 21a at a seal portion 21b on a peripheral edge thereof, so as to form a bag-like shape. A reservation space 21c for reserving collected blood is formed in the interior side space, surrounded by the seal portion 21b of the blood collection bag 21. Further, two openings 21d are formed at an upper portion of the blood collection bag 21, which are detachably sealed by a peel tab. An anticoagulant such as, for example, heparin sodium solution, ACD-A solution, CPD solution or CPD-A solution, may be placed in the reservation space 21c in advance. One or a plurality of other bags may be connected to the blood collection bag 21, by one or more tubes. A branch tube for collecting blood for inspection may be connected at a midway position of the tube 13.

Figure 2:
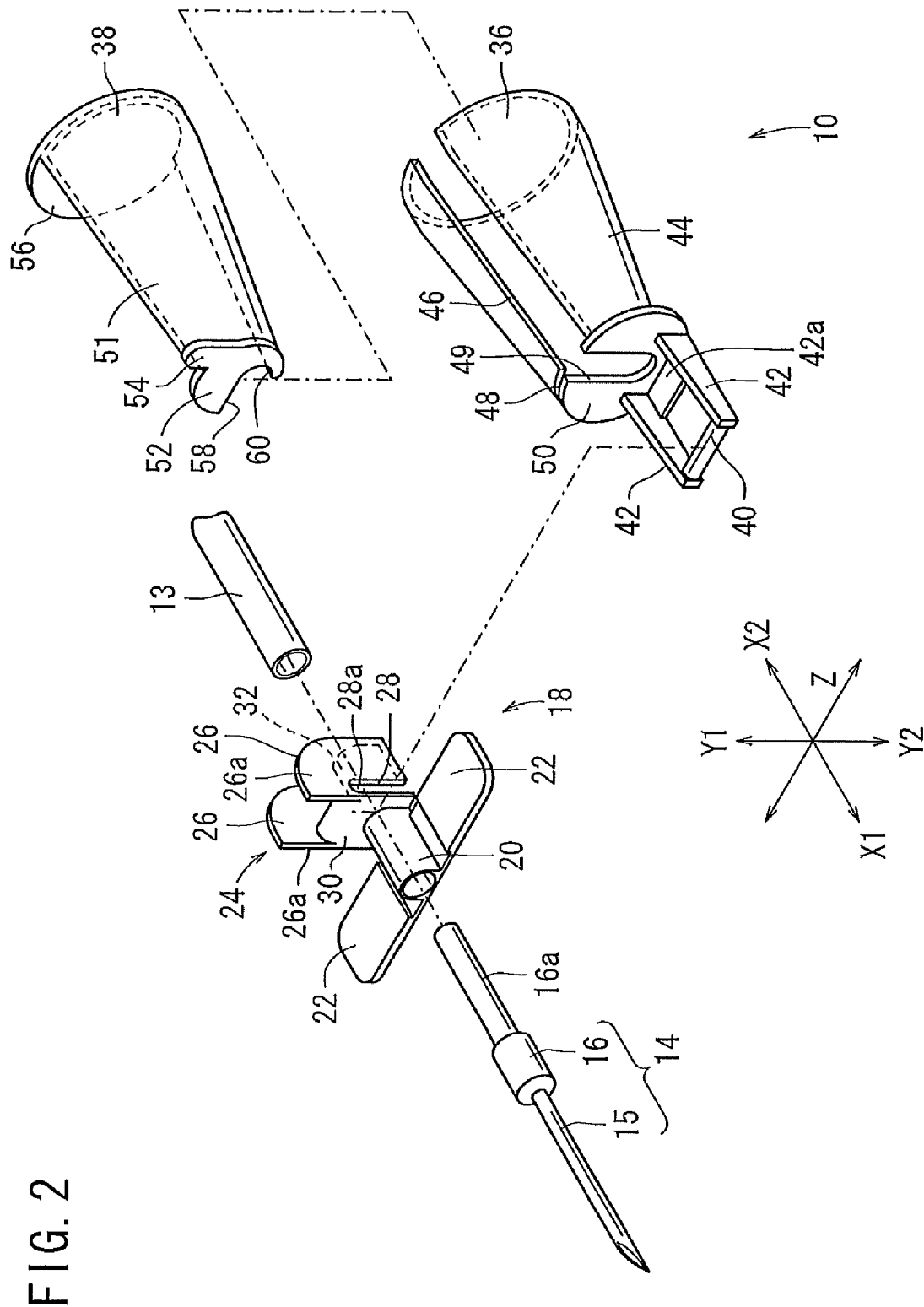
FIG. 2 is an exploded perspective view of a protector according to a first embodiment.
Figure 3:
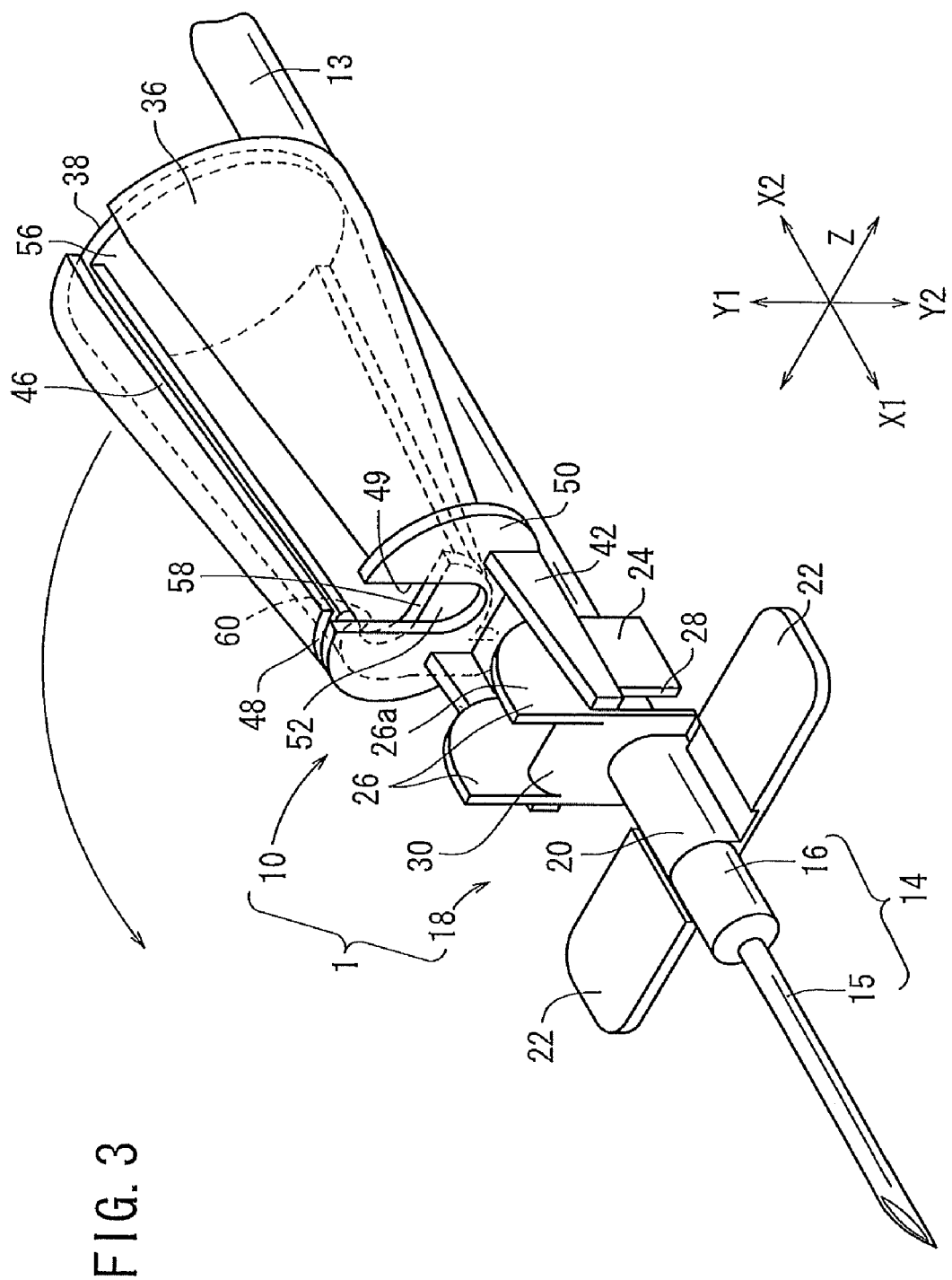
FIG. 3 is a perspective view of the protector according to the first embodiment.

As shown in FIGS. 2 and 3, the needle assembly 14 includes a needle main body 15, and a hub 16 having a multi-stage cylindrical shape for connecting the needle main body 15 to the tube 13. The needle main body 15 comprises a hollow needle, which is made of a metal such as stainless steel, aluminum or titanium, or a hard resin such as polyphenyl sulfide. In the following description, the direction X1 shown in FIG. 2 is referred to as a forward direction, whereas the opposite direction X2 is referred to as a backward direction. The end portion of the needle assembly 14 is referred to as a rear end. The direction Y1 shown in FIG. 2 is referred to as an upward direction, whereas the opposite direction Y2 is referred to as a downward direction. Further, the widthwise direction shown in FIG. 2 is referred to as a Z direction. With respect to the tilting member (protector main body 10), an end thereof which is proximate to the center of tilting motion is referred to as a proximal end side, and an end thereof remote from the center of tilting motion is referred to as a distal end side. These directional definitions are given merely for facilitating description of the invention, and in actual use, the direction of use thereof is not restricted to any particular direction.

The supporting member 18 has a tube portion 20 into which a rear hollow member 16*a* of the hub 16 is inserted, elastic wing portions 22 provided on left and right sides of the tube portion 20, and a protector supporting portion 24 disposed rearwardly of the tube portion 20. The protector supporting portion 24 has a pair of left and right ear piece portions 26, a shaft cutaway portion 28 provided in each of the ear piece portions 26, a first arch portion 30 for covering the front and upper sides of the left and right shaft cutaway portions 28, and a second arch portion 32 extending in an axial direction rearwardly of the first arch portion 30. The first arch portion 30 and the second arch portion 32 are disposed in directions differing 90° from each other.

The hollow member 16*a* has a diameter into which the hollow member 16*a* can be inserted inside of the tube 13. When the hollow member 16*a* is inserted into the tube 13, the rear end of the needle main body 15 communicates with the tube 13.

The shaft cutaway portions 28 extend to a position a little higher than the tube portion 20, as viewed in side elevation. The tube portion 20 opens forwardly and backwardly, and a rear end portion of the hollow member 16*a* extends through the tube portion 20, and reaches the rear end of the protector supporting portion 24. The tube portion 20 rotatably supports the hollow member 16*a*. The second arch portion 32 has a substantially semicircular cross section, having an arc in diameter equal to the outer diameter of the tube 13. The second arch portion 32 is disposed between the left and right ear piece portions 26.

The distance between the left and right ear piece portions 26 is substantially equal to the outer diameter of the tube 13. A portion of each of the ear piece portions 26, which is higher than the second arch portion 32, has an arcuate shape over approximately 90°, centered at a top portion 28*a* of the shaft cutaway portions 28, and a portion of the ear piece portions 26, which is lower than the second arch portion 32, has a plate-shaped form for holding a side face of the tube 13.

By fitting the hollow member 16*a* of the hub 16 into the tube portion 20, and by inserting and fixing a portion of the hollow member 16*a*, which projects from the tube portion 20, into the tube 13, the needle main body 15 is held rotatably by the supporting member 18, and the tube 13 is supported by the second arch portion 32 and lower portions of the left and right ear piece portions 26. A gap into which a shaft member 40 can be inserted is assured at the top portion 28*a* of the shaft cutaway portions 28.

The protector 1 has an outer cover member 36, which is tiltably provided for movement in a direction of the needle main body 15 with respect to the supporting member 18, and an inner cover member 38, which is disposed on the inner side of the outer cover member 36.

The outer cover member 36 has two arms 42 pivotally supported on the supporting member 18 by the shaft member 40, and a cylindrical body 44 provided on the free end side of the arms 42 for covering the needle main body 15. The outer cover member 36 preferably has a suitable strength and can be formed, for example, from a material such as polycarbonate or the like. The number of such arms 42 may also be one, for example. In this instance, the arm 42 should be provided between the ear piece portions 26.

The shaft member 40 connects the proximal end portions of the two arms 42 to each other. The shaft member 40 has a diameter which enables it to be fitted into the top portions 28*a*. Further, before the hollow member 16*a* of the needle assembly 14 is fitted into the tube portion 20, the shaft member 40 is fitted from below into the shaft cutaway portions 28. Consequently, the tube 13 is capable of tiltably supporting the shaft member 40 and the arms 42 while closing a portion of the shaft cutaway portions 28. Also, the shaft member 40 serves as the center of pivotal motion of the outer cover member 36. Consequently, the mechanism for pivotally supporting the outer cover member 36 can be implemented simply and readily, and assembly of the mechanism is easy.

The two arms 42 are provided in a spaced relationship from each other by a given distance, such that the inner side faces of the two arms 42 contact the left and right side faces (supporting faces) 26*a* of the ear piece portions 26, whereby the outer cover member 36 can be tilted stably. A reinforcing plate 42*a* is disposed at a position between the two arms 42, so as not to interfere with the ear piece portions 26.

The cylindrical body 44 includes a needle slit 46 into which the needle main body 15 is fitted at a position displaced to one side from the center, and which extends in an axial direction. The cylindrical body 44 further includes a circumferential slit 48 extending substantially 180° in the circumferential direction, and an outer bottom 50, which closes the proximal end side, except for a cutaway portion 49 through which the hub 16 of the needle main body 15 passes. The width of the cutaway portion 49 is substantially equal to the outer diameter of the hub 16. The amount at which the needle slit 46 is displaced from the center of the cylindrical body 44 defines a distance L (refer to FIG. 6). The cylindrical body 44 has a conical shape, which expands toward the distal end thereof. The circumferential slit 48 is disposed on the most proximal end side of the cylindrical body 44, and communicates at one end thereof with the needle slit 46.

The inner cover member 38 has an arcuate column (shield plate) 51, an inner bottom 52 provided on the proximal end side of the arcuate column 51, a projection 54 for engaging with the circumferential slit 48, and a lid member 56 for closing the front end. The lid member 56 may be provided on the outer cover member 36. In this instance, the lid member 56 may be mounted externally on the outer cover member 36, after the inner cover member 38 has been inserted into the outer cover member 36. Owing to the presence of the lid member 56, leakage of blood from the needle main body 15 can be prevented with a higher degree of certainty.

The inner cover member 38 preferably has a suitable strength, having a property that prevents slippage with respect to the outer cover member 36. The inner cover member 38 can be made from a material such as, for example, polypropylene, polyethylene, or the like.

The arcuate column 51 slides and rotates on the inner face of the cylindrical body 44 in an interlocking relationship with the needle main body 15, when the outer cover member 36 is tilted and the needle main body 15 is inserted into the needle slit 46. The arcuate column 51 has a shape which expands toward an end thereof, in conformity with the inner face of the cylindrical body 44. The lengths of the arcuate column 51 and the cylindrical body 44 are equal to each other in the axial direction.

The arcuate column 51 has an arcuate sectional shape, which is open at least at an area thereof that faces the needle slit 46, when the inner cover member 38 is in an opening position with respect to the cylindrical body 44. The arcuate column 51 closes the needle slit 46 in a closing position. The opening position of the inner cover member 38 defines a position of a state in which the projection 54 is disposed at an end portion of the circumferential slit 48. When the needle main body 15 prior to use thereof is taken out from its accommodated state, the inner cover member 38 assumes a rotation end position. However, when the needle main body 15 is to be accommodated after use thereof, the inner cover member 38 assumes an initial position. The closing position of the inner cover member 38 defines a position of another state, in which the projection 54 is disposed substantially in the middle of the circumferential slit 48. When the needle main body 15 is to be taken out from its accommodated state after use thereof, the inner cover member 38 assumes the initial position. However, when the needle main body 15 is to be accommodated after use thereof, the inner cover member 38 assumes the rotation end position.

The inner bottom 52 has a needle receiving edge portion 58 and a detachment preventing end portion 60. The needle receiving edge portion 58 and the detachment preventing end portion 60 have a J shape (or a hook shape). The needle receiving edge portion 58 forms the straight portion of the J shape. When the inner cover member 38 is in the opening position, the needle receiving edge portion 58 crosses (substantially perpendicularly) with respect to the cutaway portion 49. However, when the outer cover member 36 is tilted and the needle main body 15 is inserted into the needle slit 46 and the cutaway portion 49, the needle receiving edge portion 58 is pushed down by the needle assembly 14. The detachment preventing end portion 60 defines a portion which closes the open side of the cutaway portion 49, and which prevents detachment of the needle assembly 14 when the inner cover member 38 is placed in the closing position. The detachment preventing end portion 60 forms the curved portion of the J shape. The shape of the location, which corresponds to the detachment preventing end portion 60, is not limited to a curved shape but also may be a bent shape or the like.

When the inner cover member 38 is assembled onto the outer cover member 36, the arcuate column 51 is inserted into the cylindrical body 44, with the projection 54 being fitted in the needle slit 46 (in the assembled position). Then, after the projection 54 arrives at the position of the circumferential slit 48, the inner cover member 38 is rotated in a circumferential direction by approximately 180°. Consequently, the outer cover member 36 and the inner cover member 38 can be produced separately from each other. Further, except for the assembled position, in which the projection 54 is disposed in the needle slit 46, the projection 54 remains in engagement with the circumferential slit 48, within a range from the opening position to the closing position of the inner cover member 38, and the inner cover member 38 is guided in the circumferential direction so that the inner cover member 38 does not come off from the outer cover member 36. The projection 54 projects slightly from the circumferential slit 48.

Figure 6:
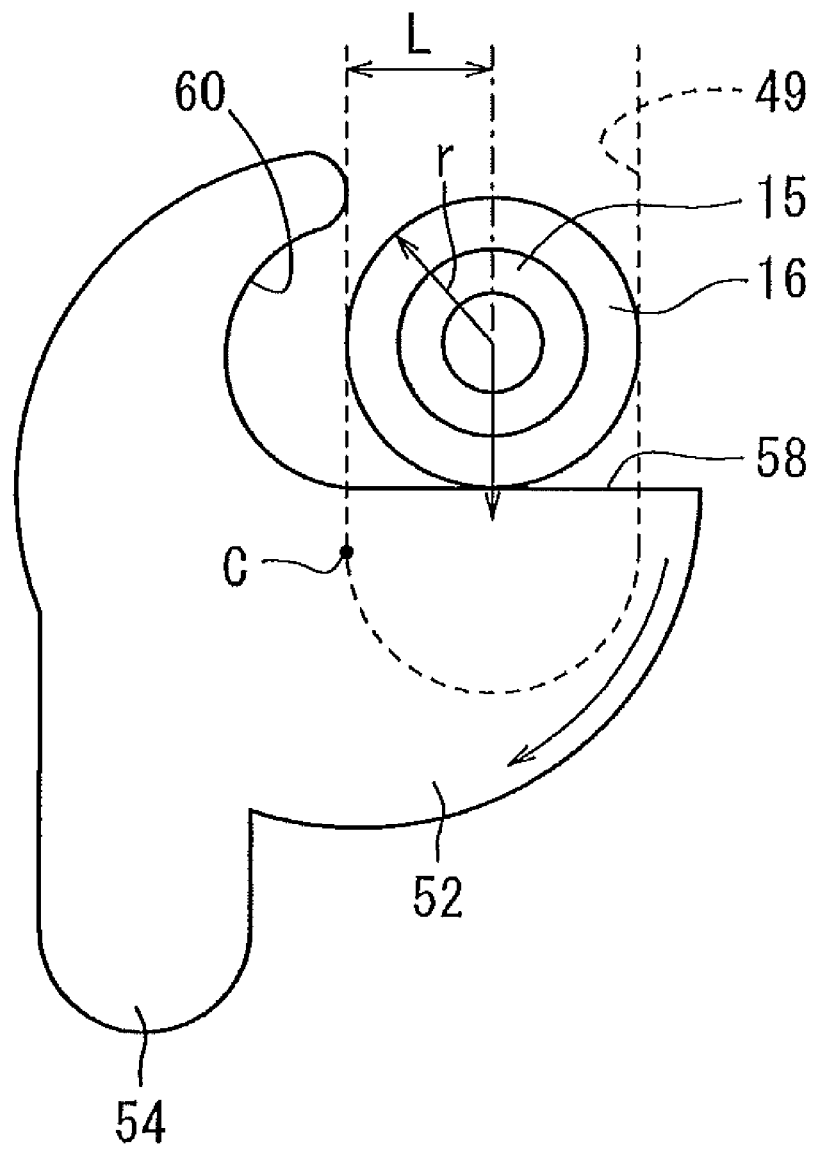
FIG. 6 is an explanatory view illustrating a positional relationship between a needle and an inner bottom, when the hub in the protector according to the first embodiment contacts the needle receiving edge portion.

Further, since the needle slit 46 is provided at a position displaced to one side (offset) from the center, when the needle assembly 14 (hub 16) is brought into contact with the needle receiving edge portion 58 of the inner bottom 52, the needle receiving edge portion 58 is pushed down, and the arcuate column 51 is acted upon by a torque and can rotate (refer to FIG. 6). Further, when the arcuate column 51 reaches the closing position, the detachment preventing end portion 60 has a J shape, and thus can prevent detachment of the needle assembly 14 (refer to FIG. 11).

Next, operations of the aforementioned protector 1, which is configured in the foregoing manner, shall be described. In the protector 1, the needle main body 15 is initially covered with the protector main body 10, whereby the needle main body 15 can be prevented from being touched arbitrarily. Further, with the protector 1, since there is no need for a separately-provided cap for accommodating the needle main body 15 therein prior to use, waste can be reduced.

Figure 10:
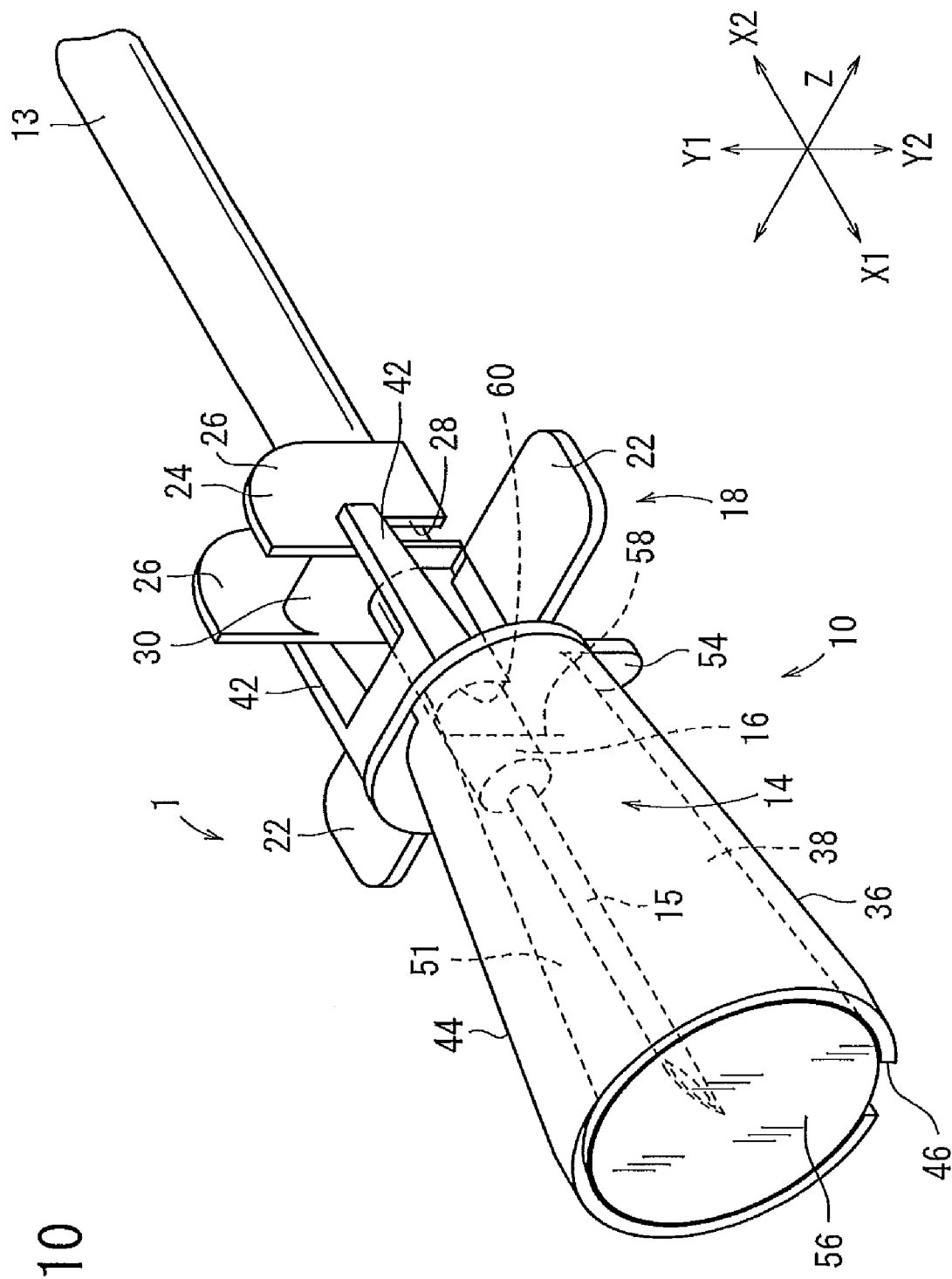
FIG. 10 is a perspective view illustrating a state in which the hub in the protector according to the first embodiment pushes down vertically on the needle receiving edge portion.

First, the protector 1 in an operational state, in which the protector main body 10 shown in FIG. 10 covers the needle main body 15, is placed in a standby state, wherein the protector main body 10 shown in FIG. 3 is exposed from the needle main body 15.

When an operator, such as a medical professional, moves the projection 54 along the circumferential slit 48, the inner bottom 52 of the inner cover member 38 rotates, and the hub 16 of the needle main body 15 comes off from the detachment preventing end portion 60 of the inner cover member 38, and moves along the cutaway portion 49 of the outer cover member 36. Consequently, the arcuate column 51 of the inner cover member 38 moves from the closing position, in which the arcuate column 51 closes the needle slit 46 of the outer cover member 36, to the opening position, in which the arcuate column 51 of the inner cover member 38 does not overlap the needle slit 46 of the outer cover member 36, thereby to open the needle slit 46.

In this state, since the cylindrical body 44 of the outer cover member 36 has a conical shape whose diameter increases toward the distal end side, the needle main body 15 is positioned in the inside of the outer cover member 36. This state is the same as a state (refer to FIG. 5) in which the hub 16 of the needle main body 15 contacts the needle receiving edge portion 58 of the inner cover member 38, when the needle main body 15 is accommodated again, as shall be described later. Therefore, the protector 1 is configured such that the operator is restrained or prevented from touching the needle main body 15.

Then, the arms 42 of the outer cover member 36 are tilted in a direction toward the hub 16 (tube 13) around the shaft member 40, so as to establish a state in which the protector main body 10 is positioned upward or rearward with respect to the tube 13.

Thereafter, the needle main body 15 is made to penetrate into a vein (blood vessel) of a donor (including a patient) to carry out blood collection. The collected blood is accommodated from the needle assembly 14 into the blood collection bag 21 through the tube 13.

During blood collection, the elastic wing portions 22 can be kept fixed to an arm or the like of the donor. Further, the arms 42 of the protector main body 10 are held in contact with left and right side faces 26*a* of the pair of ear piece portions 26. Consequently, blood collection can be carried out in a stable state. In order to appropriately acquire blood, the needle assembly 14 may be rotated with respect to the supporting member 18 in order to adjust the direction. After blood collection is completed, the needle main body 15 is pulled out from the arm of the donor.

Then, the protector main body 10 is tilted (pivoted) about the shaft member 40, so as to fall downward in the direction of the needle main body 15. At this time, the arms 42 are kept in contact with left and right side faces 26*a* of the pair of ear piece portions 26, and tilting movement thereof can be carried out in a stable state.

Figure 4:
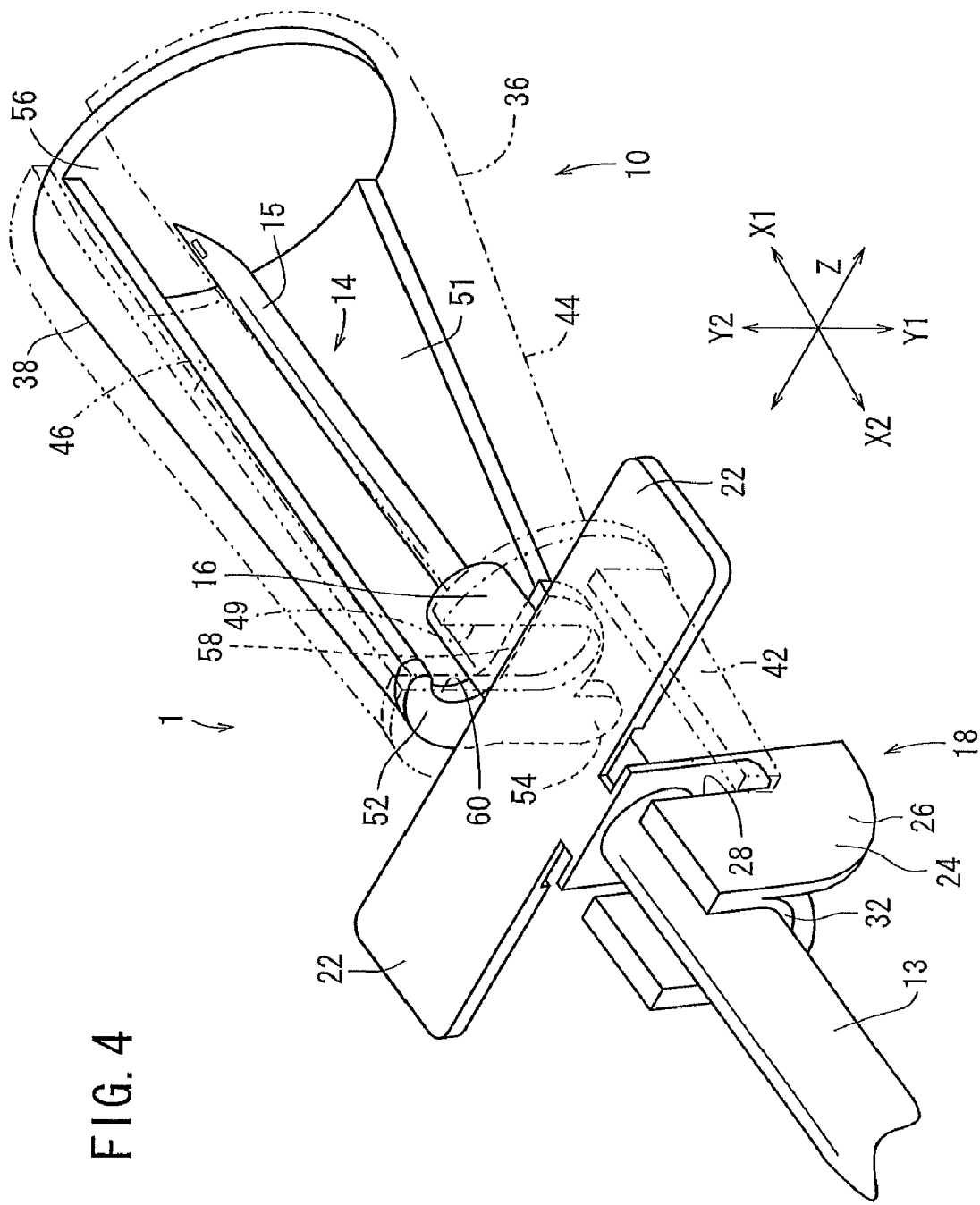
FIG. 4 is a perspective view with partial omission, showing a state in which a hub in the protector according to the first embodiment contacts with a needle receiving edge portion.
Figure 5:
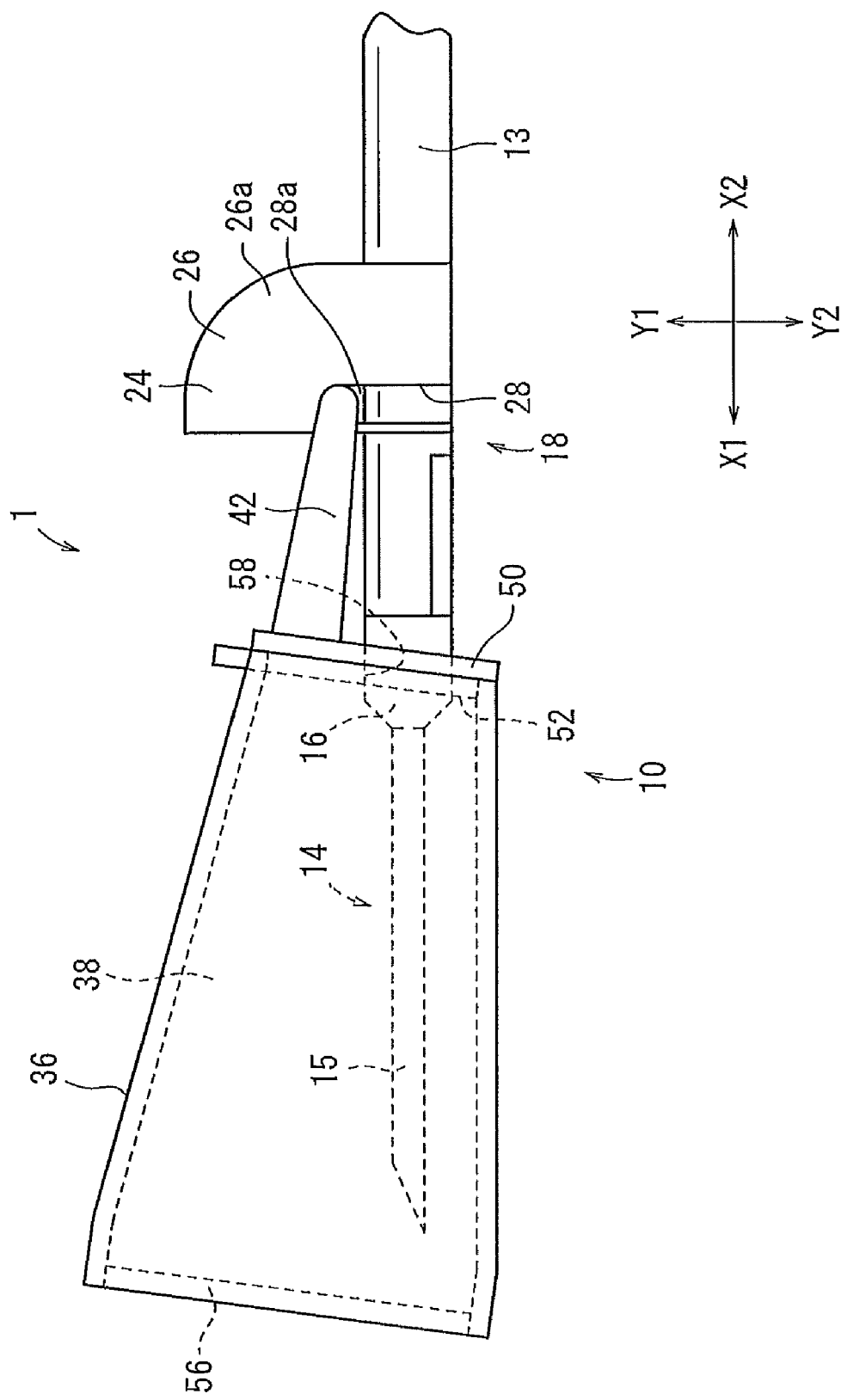
FIG. 5 is a side elevational view showing a state in which the hub in the protector according to the first embodiment contacts with the needle receiving edge portion.

As shown in FIG. 4, when the outer cover member 36 is tilted, the hub 16 of the needle main body 15 is brought into contact with the needle receiving edge portion 58 of the inner cover member 38. It shall be assumed that the needle receiving edge portion 58 initially is in a horizontal state. In FIGS. 4, 6, 7 and 8, the inner cover member 38 is shown in a state as viewed from below in order to facilitate understanding of the direction of the inner cover member 38. The outer cover member 36, the needle slit 46, and the cutaway portion 49 are indicated by imaginary lines.

Since the needle slit 46, through which the needle main body 15 passes, is provided at a position displaced from the center by the distance L in the Z direction (i.e., a direction perpendicular to the direction in which the needle passes), when the hub 16 is brought into contact with the needle receiving edge portion 58 of the inner bottom 52, the needle receiving edge portion 58 is pushed down thereafter, and the arcuate column 51 begins to rotate in a clockwise direction, as shown in FIG. 4, from the opening position to the closing position.

Since the cylindrical body 44 and the arcuate column 51 have a conical shape (more precisely, a circular conical truncated shape), which expands toward the distal end thereof, at a point in time when the outer cover member 36 is tilted and until the hub 16 is brought into contact with the needle receiving edge portion 58 of the inner cover member 38, the needle main body 15 conveniently is covered in its entirety (or almost completely), with the outer cover member 36 as viewed in side elevation.

Incidentally, since the hub 16 presses the needle receiving edge portion 58 by a distance L as seen in FIG. 6, and the arcuate column 51 rotates with reference to the center C in order to apply sufficient torque to the needle receiving edge portion 58, preferably the distance L should be great. On the other hand, if the distance L is too great, then the protector 1 has an increased size, and the amount of movement when the hub 16 pushes down the needle receiving edge portion 58 becomes great. Accordingly, the distance L should have an appropriate range, such that when the radius r of a portion of the hub 16 which passes the cutaway portion 49 is taken as a reference, the distance L preferably falls within a range of r/2≦L≦2r.

Figure 7:
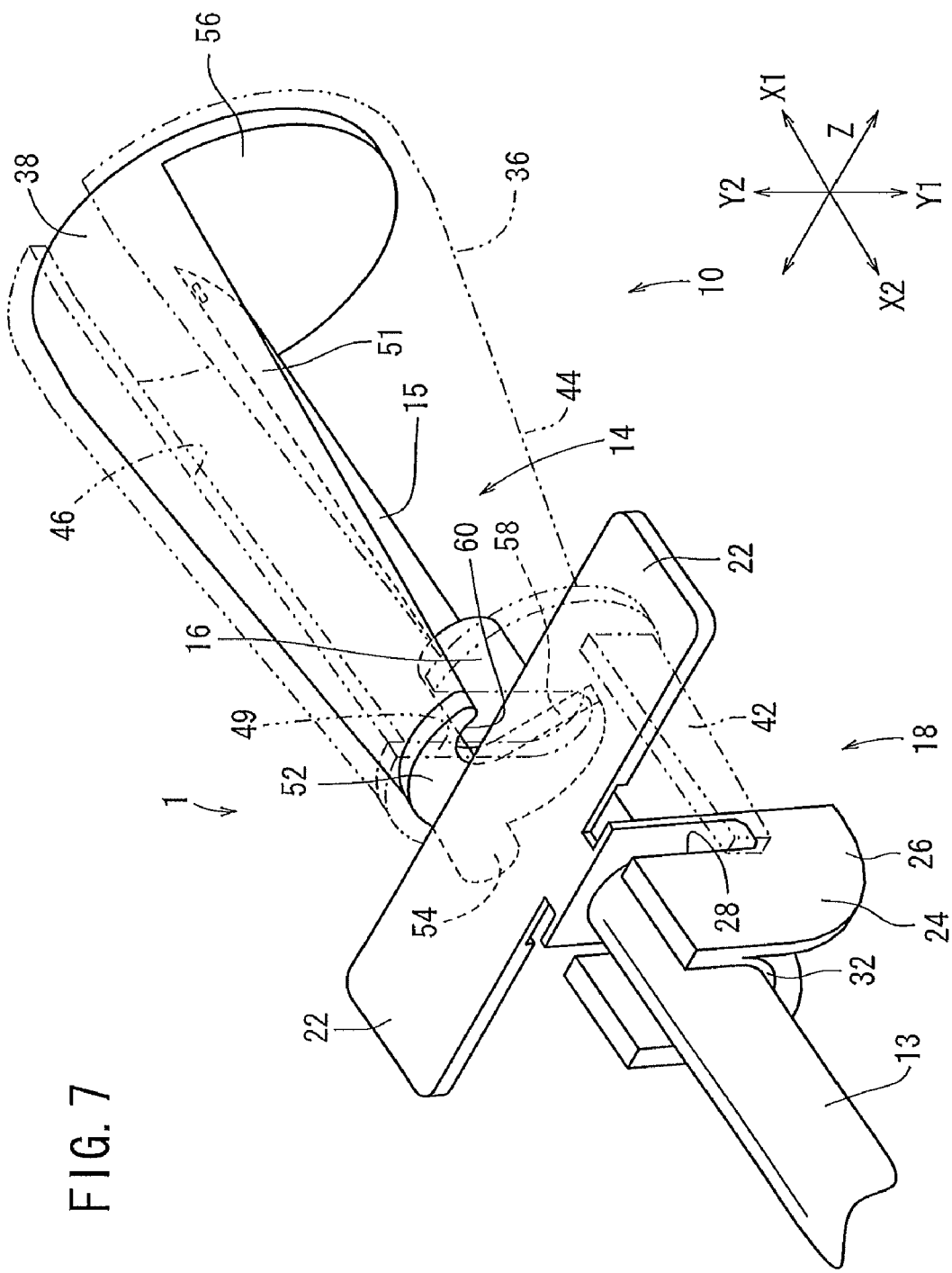
FIG. 7 is a perspective view with partial omission, illustrating a state in which the hub in the protector according to the first embodiment pushes down obliquely on the needle receiving edge portion.

If the outer cover member 36 is tilted further so as to fall down as shown in FIG. 7, then the hub 16 presses the needle receiving edge portion 58 in order to rotate the arcuate column 51 and the inner cover member 38, and the needle receiving edge portion 58 is brought into an oblique position.

Figure 8:
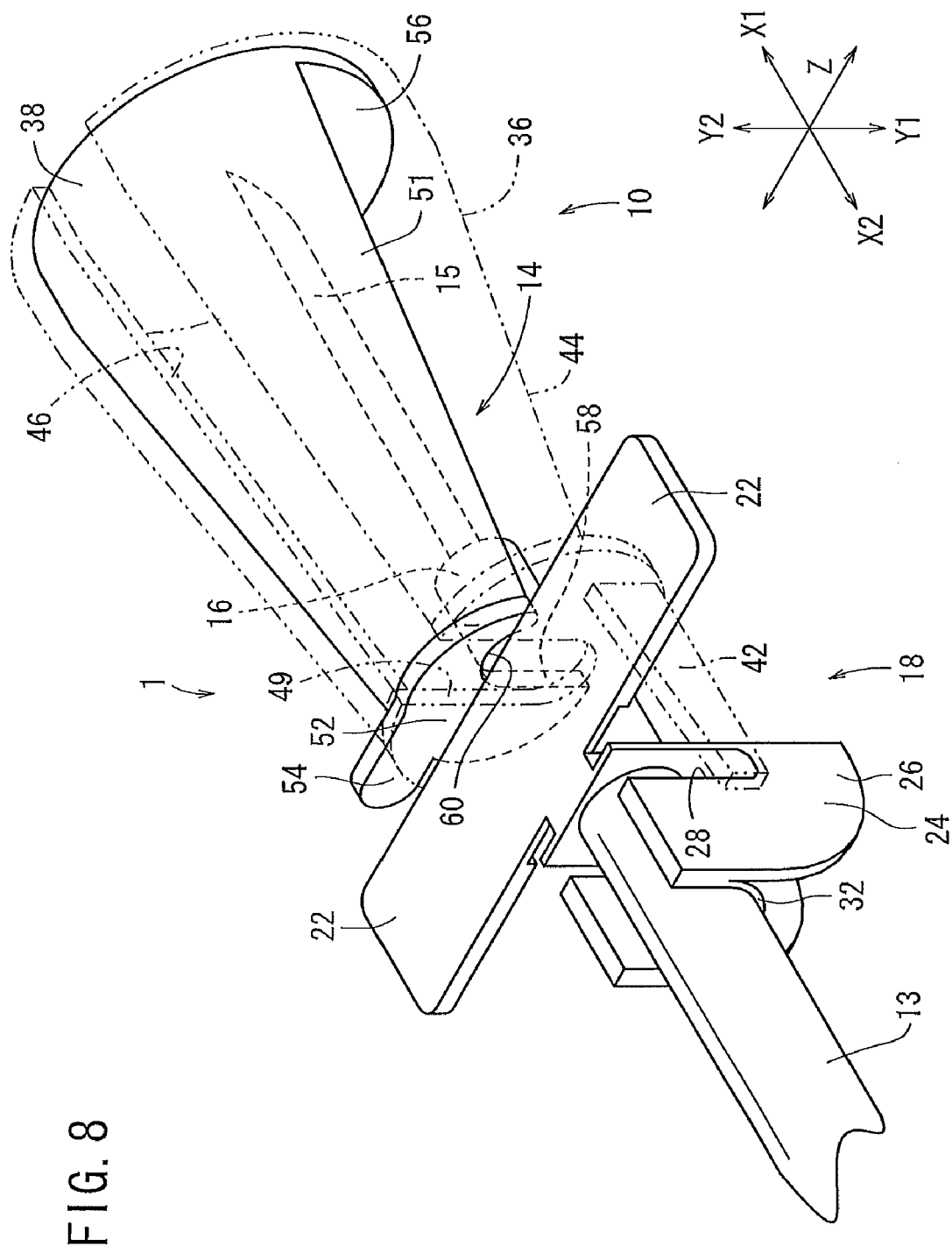
FIG. 8 is a perspective view with partial omission, illustrating a state in which the hub in the protector according to the first embodiment pushes down vertically on the needle receiving edge portion.

If the outer cover member 36 is tilted further so as to fall down as shown in FIG. 8, then the hub 16 presses the needle receiving edge portion 58 so that the arcuate column 51 and the inner cover member 38 reach the closing position, and the needle receiving edge portion 58 is directed in a vertical direction. Finally, the inner cover member 38 reaches the closing position, by rotating approximately 90° from the opening position.

Figure 9:
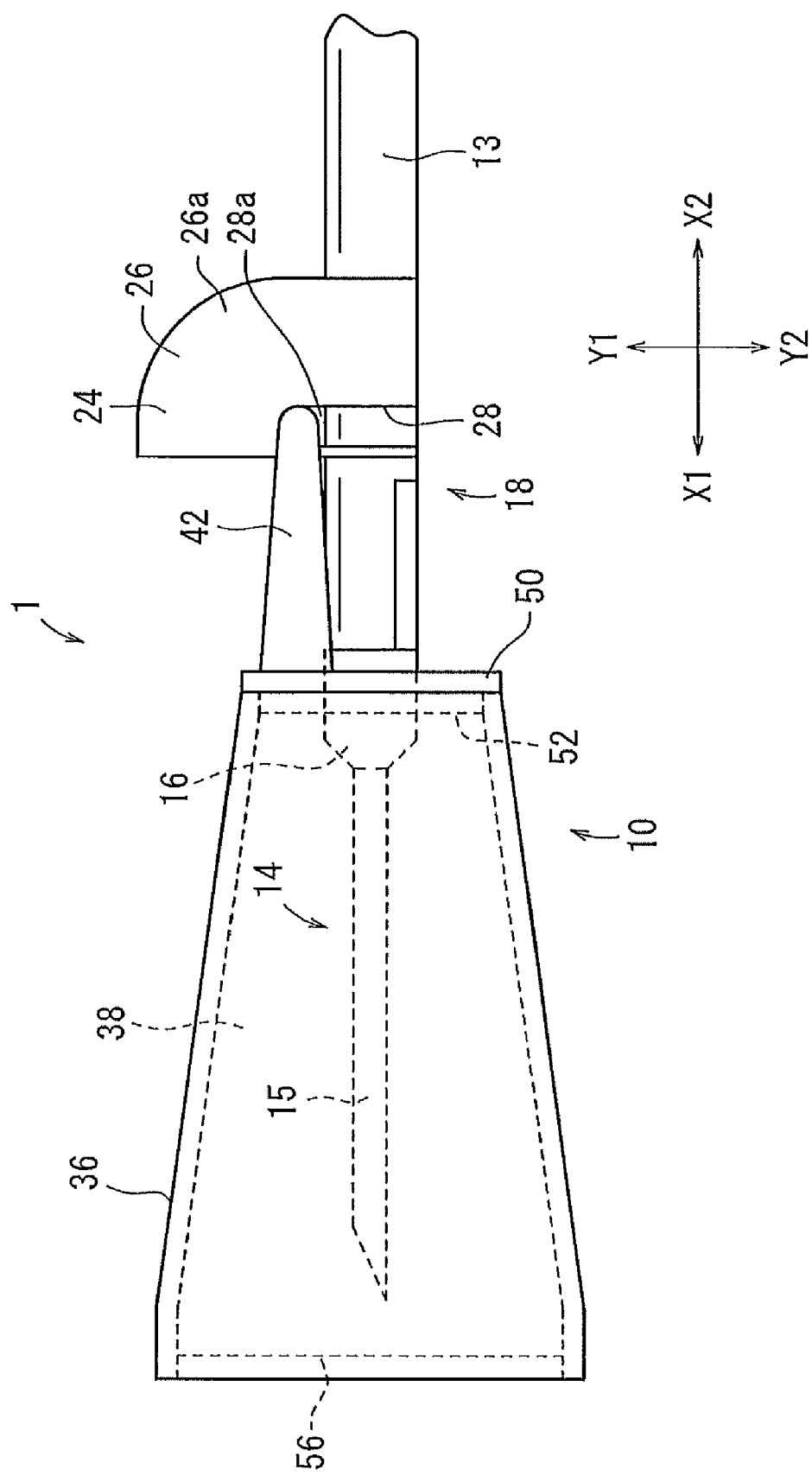
FIG. 9 is a side elevational view illustrating a state in which the hub in the protector according to the first embodiment pushes down vertically on the needle receiving edge portion.

Consequently, as shown in FIGS. 9 and 10, the needle main body 15 is covered over the entire circumference thereof with the outer cover member 36 and the inner cover member 38 of the protector main body 10, and is covered at the distal end thereof with the lid member 56. Further, the needle main body 15 is covered on a proximal end side thereof with the outer bottom 50 and the inner bottom 52. Consequently, leakage of blood can be prevented considerably. Further, the needle main body 15 can be prevented from being touched inadvertently. Also, when the needle main body 15 is to be accommodated after use thereof, a state of transition occurs in the order of FIGS. 5, 7 and 8. However, when the needle main body 15 is to be taken out after use thereof, the projection 54 is operated, and naturally, a state of transition occurs in the order of FIGS. 8, 7 and 5.

Figure 11:
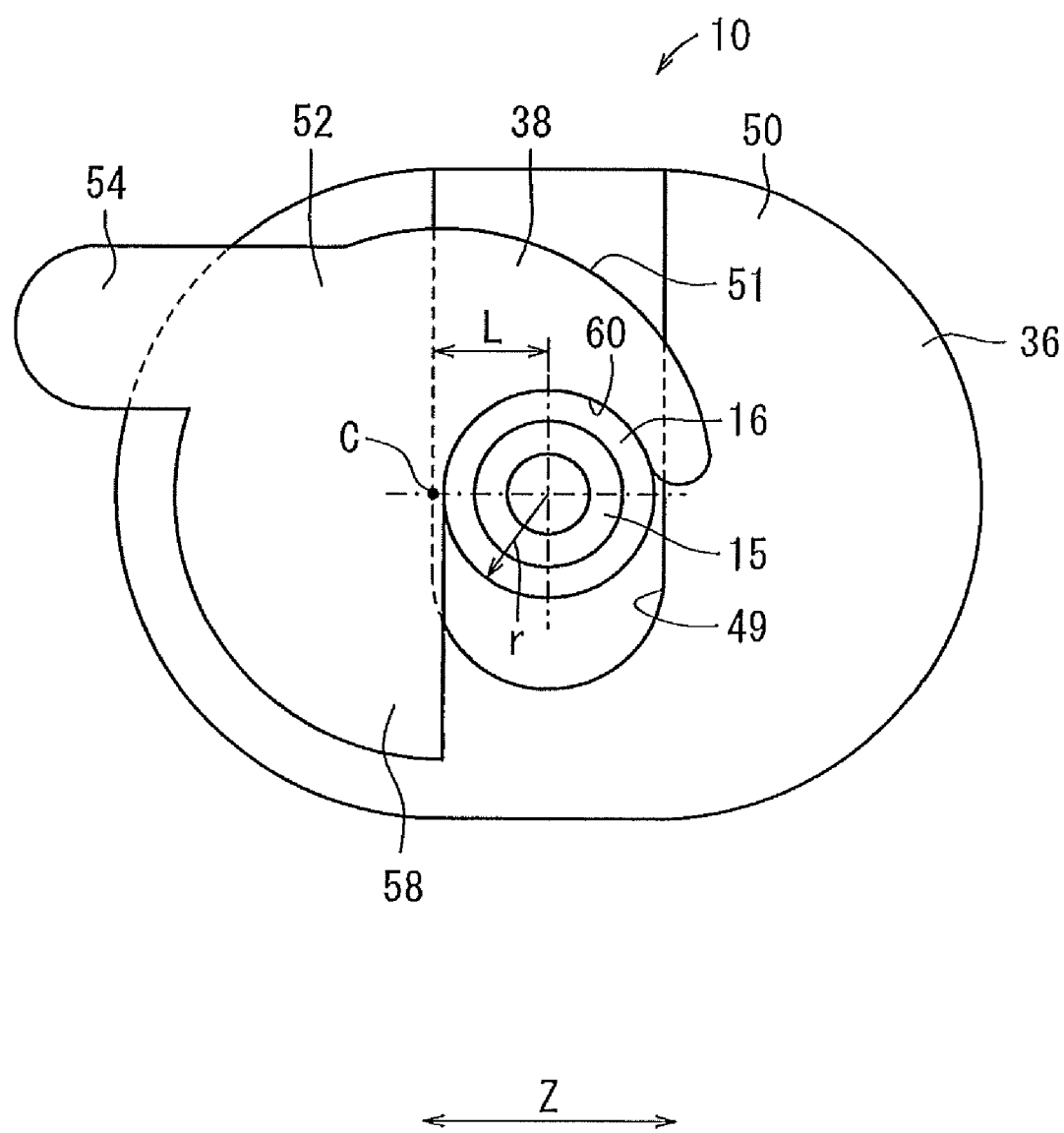
FIG. 11 is an explanatory view illustrating a positional relationship between the needle and the inner bottom when the hub in the protector according to the first embodiment pushes down vertically on the needle receiving edge portion.

If the inner cover member 38 is placed in the closed state, as shown in FIG. 11, then the detachment preventing end portion 60 covers an upper half of the hub 16. Even if force is applied so as to return the protector main body 10 to the original position, the hub 16 is caught by the detachment preventing end portion 60, and the inner cover member 38 hardly rotates, whereby the needle assembly 14 can be prevented from becoming detached from the protector main body 10. In particular, although the hub 16 applies a moment corresponding to the distance L to the inner cover member 38, and the inner cover member 38 rotates slightly in a counterclockwise direction as shown in FIG. 11, since the detachment preventing end portion 60 has a hook shape, it is caught by the hub 16, and the inner cover member 38 is prevented from rotating further. In other words, the needle assembly 14 (hub 16) is locked by the detachment preventing end portion 60 of the inner bottom 52.

Figure 12:
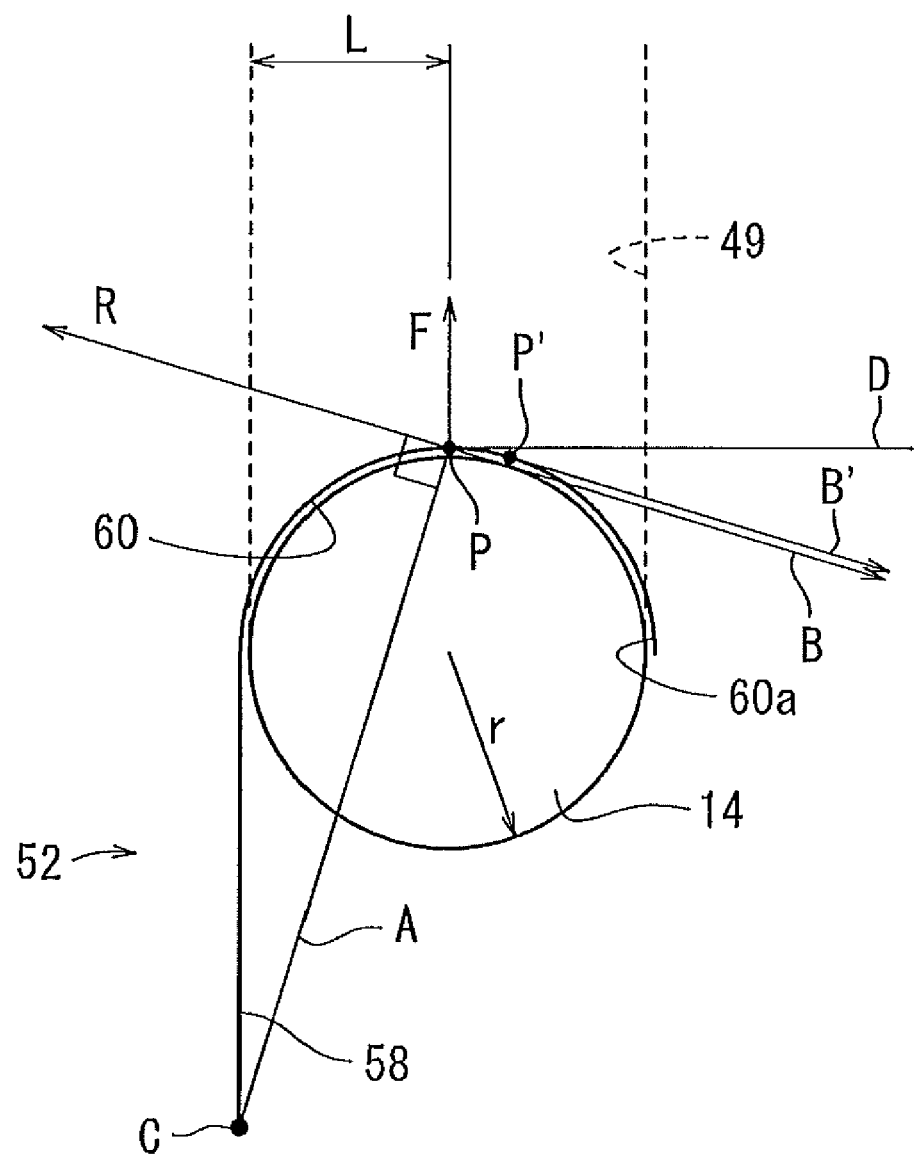
FIG. 12 is a dynamic schematic view illustrating a force applied by the needle to the needle receiving edge portion, on an inner bottom and a detachment stopping end portion thereof.

The above-described locking configuration shall be described in greater detail below with reference to FIG. 12. FIG. 12 is a dynamic schematic view illustrating forces applied from the needle assembly 14 to the needle receiving edge portion 58 and to the detachment preventing end portion 60 of the inner bottom 52.

Referring to FIG. 12, reference character C denotes a center of rotation of the inner bottom 52, P denotes a representative point of action at which the needle assembly 14 applies force to the inner bottom 52, A denotes a line segment interconnecting the center C and the point of action P, R denotes a vector in a direction in which the point of action P tends to rotate, and F denotes a vector of force applied to the inner bottom 52 from the needle main body 15.

If a force represented by the vector F is applied to the detachment preventing end portion 60, then the point of action P tends to rotate in the direction of a vector R. The vector F is directed toward the opening of the cutaway portion 49 (refer to FIG. 11) and is directed upwardly, as shown in FIG. 12. The vector R is directed in an oblique lefthand-upward direction in FIG. 12, at a right angle with respect to the line segment A. A vector B is defined whose base point is the point of action P and the direction of which is opposite to that of the vector R. Another vector is defined as a vector B' when the vector B is moved parallel to the line segment A toward an end point P' of the detachment preventing end portion 60. As made apparent from FIG. 12, the vectors B and B' are directed in an oblique righthand-downward direction.

Incidentally, at the point of action P, a tangential line D to the detachment preventing end portion 60 is substantially horizontal, and detachment prevention of the needle assembly 14 cannot be achieved only by this portion. This is because the gradient of the tangential line D is more moderate than that of the vector B', and nothing forms an obstacle to movement of the point of action P in the direction of the vector R.

However, the distal end portion 60a of the detachment preventing end portion 60 beyond the end point P' has a gradient greater than that of the vector B', and prevents the point of action P from moving in the direction of the vector R. This is because if a force represented by the vector F acts thereon, then although the distal end portion 60a tends to move in the direction of the vector R, the distal end portion 60a comes into contact with and is stopped from moving further by a given portion of the needle assembly 14. In this manner, the inner bottom 52 can be prevented from rotating by the detachment preventing end portion 60.

In other words, rotation of the inner bottom 52 can be prevented if the point P' of the needle assembly 14, which is remotest as viewed from the center C, is taken as a reference, and the detachment preventing end portion 60 is positioned closer to the center O than the end point P' on the opposite side in the rotation direction (in the righthand-downward direction illustrated in FIG. 12).

This description of the principle of the lock mechanism is provided as an example, and descriptions thereof may naturally be presented based on other principles. For example, a description may be given assuming that the vector F acts upon the end point P'.

As described above, when the protector 1 according to the first embodiment is tilted only in one direction, the arcuate column 51 of the inner cover member 38 rotates in an interlocking relationship with the needle assembly 14, and can automatically cover the needle slit 46 after the needle main body 15 passes therethrough. Consequently, the needle main body 15 is covered with the protector main body 10 and operation thereof is easy. Such an operation can be carried out simply and conveniently using only one hand. Under ordinary use, the outer cover member 36 and the inner cover member 38 are not separated from each other, and handling thereof is easy. Further, with the protector 1, the needle main body 15 can be kept in a covered state prior to use thereof.

Next, a protector 100 according to a second embodiment shall be described.

Figure 13:
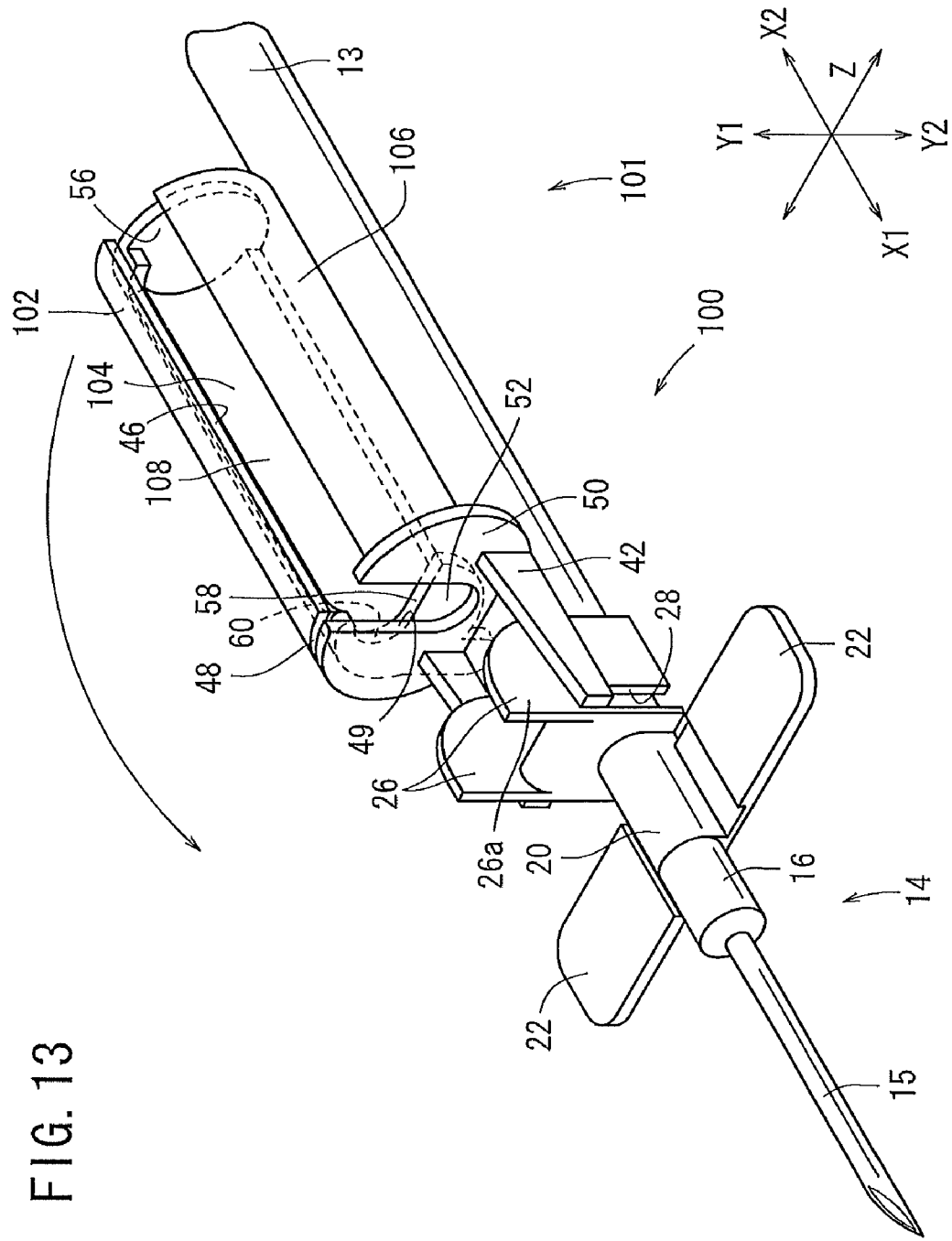
FIG. 13 is a perspective view of a protector according to a second embodiment.

As shown in FIG. 13, the protector 100 includes a protector main body 101, and a supporting member 18. The protector main body 101 includes an outer cover member 102 and an inner cover member 104. The outer cover member 102 and the inner cover member 104 correspond with the outer cover member 36 and the inner cover member 38. In the protector 100, components thereof which are the same as those of the protector 1 described above are denoted by like reference characters, and detailed descriptions of such features are omitted.

A cylindrical body 106 of the outer cover member 102 forms a member that corresponds to the above-described cylindrical body 44 and has a cylindrical shape with a substantially fixed diameter.

An arcuate column (masking shield plate) 108 forms a member that corresponds to the above-described arcuate column 51. When the outer cover member 102 is tilted and the needle main body 15 is inserted into the needle slit 46, the arcuate column 108 slides along the inner face of the cylindrical body 44 and rotates in an interlocking relationship with the needle main body 15. The arcuate column 108 has an arcuate shape of a substantially fixed diameter, conforming to the inner face of the cylindrical body 106. The lengths of the arcuate column 108 and the cylindrical body 106 in the axial direction are equal to each other.

Figure 14:
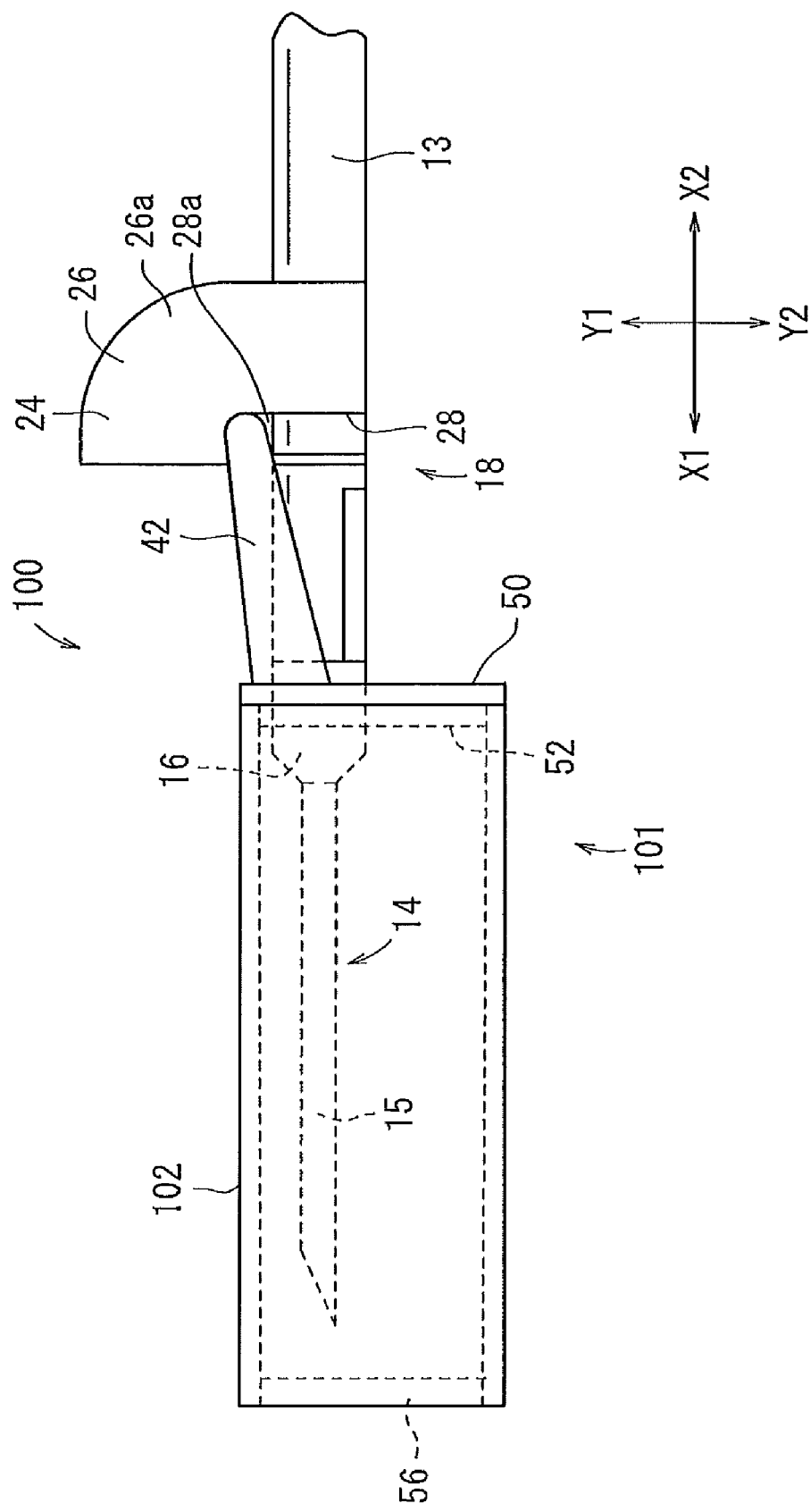
FIG. 14 is a side elevational view of a state in which a hub in the protector according to the second embodiment pushes down vertically on a needle receiving edge portion.

As shown in FIG. 14, the protector 100 is configured such that, when the protector main body 101 covers the needle main body 15 (i.e., when the arcuate column 108 moves from the opening position to the closing position), the center axis of the needle main body 15 assumes a position displaced in a Y1 direction (the direction in which the needle passes) from the center axis of the protector main body 10 (outer cover member 102). In other words, the center axis of the outer cover member 102 is disposed at a position displaced in a direction in which the needle main body 15 passes, with reference to the center axis of the inner cover member 104.

Although another configuration is possible, in which the center axis of the needle main body 15 coincides substantially with the center axis of the protector main body 101 (outer cover member 102), in this instance, since the center axis of the needle main body 15 and the center axis of the inner cover member 104 coincide with or are positioned near to each other, the cutaway portion 49 becomes shallow, and the stroke over which the needle main body 15 moves becomes short. Consequently, it is less easy for the inner cover member 104 (arcuate column 108) to slide along the inner face of the outer cover member 102 (cylindrical body 106).

Further, the inner diameter of the outer cover member 102 (cylindrical body 106) can be increased so that, while the positional relationship between the center axis of the needle main body 15 and the center axis of the inner cover member 104 is maintained (i.e., the center axis of the needle main body 15 assumes a position displaced in the Y1 direction from the center axis of the outer cover member 102), the center axis of the needle main body 15 and the center axis of the protector main body 10 (outer cover member 102) are made to coincide with each other. In this instance, however, the size of the protector main body 10 will be increased.

The protector 100 described above can achieve operations and effects similar to those of the aforementioned protector 1, and can cover the overall circumference of the needle main body 15, as shown in FIG. 14. Further, the cylindrical body 106 and the arcuate column 108 have fixed diameters, and the protector main body 101 can be made compact.

When an operator, such as a medical professional, operates the projection 54 to move the arcuate column 108 from the closing position, at which the needle slit 46 is closed, to the opening position, at which the arcuate column 108 does not overlap the needle slit 46 of the outer cover member 102 to open the needle slit 46, then the needle main body 15 passes by the needle slit 46 and becomes exposed from the protector main body 101 (outer cover member 36). Therefore, the operator can easily carry out an operation of tilting the outer cover member 102 in order to place the protector main body 101 in a standby state, in which the protector main body 101 is positioned above the tube 13.

At a point in time at which the outer cover member 102 is tilted further, and until the hub 16 is brought into contact with the needle receiving edge portion 58 of the inner cover member 104, although a portion of the needle main body 15 is not covered by the protector main body 101, the needle main body 15 becomes fully covered immediately thereafter, so as to establish the state illustrated in FIG. 14.

Figure 15:
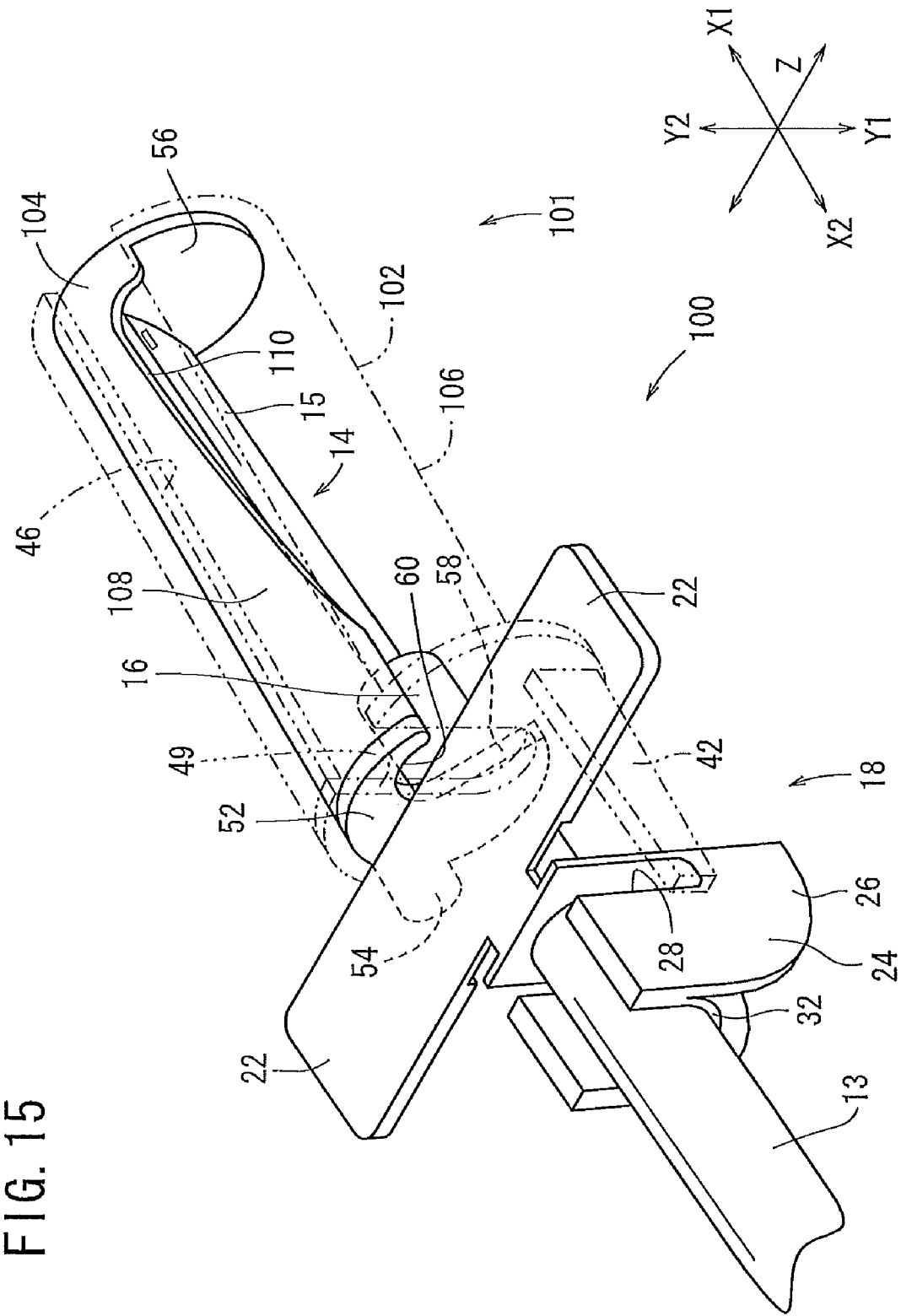
FIG. 15 is a perspective view with partial omission, showing a state in which the hub in the protector according to the second embodiment pushes down obliquely on the needle receiving edge portion.

Further, as shown in FIG. 15, the arcuate column 108 is configured such that one side 110 thereof has a moderate spiral shape, with the proximal end side being wider and the distal end side being narrower, so that the arcuate column 108 covers the needle slit 46 beginning with a position of the needle slit 46 through which the needle main body 15 passes. Consequently, the needle main body 15 can be covered by the arcuate column 108 as quickly as possible. In FIG. 15, the inner cover member 104 is shown in a state as viewed from below, so that the shape of the inner cover member 104 can be recognized easily. The outer cover member 102, the needle slit 46 and the cutaway portion 49 are indicated by imaginary lines. FIG. 15 illustrates a state corresponding to that shown in FIG. 7 in the description of the protector 1.

The protectors 1 and 100 and the protector assembly according to the above embodiments are applicable not only to the needle assembly 14 of a blood collecting device, but can also be applied naturally and suitably to other medical needles used for blood transfusion, infusion, and so forth.

Further, the arcuate columns 51 and 108, which serve as shield plates for the inner cover members 38 and 104 according to the above embodiments, may have any shape provided they can close the needle slit 46 of the outer cover members 36 and 102.

The protector and the protector assembly according to the present invention are not limited to the above-described embodiments, but can naturally be formed by adopting other various configurations, without departing from the subject matter of the present invention.

The invention claimed is:

1. A protector comprising:
   a supporting member mounted on a needle body; and
   a protector main body including an outer cover member disposed tiltably with respect to the supporting member, and an inner cover member disposed on the inner side of the outer cover member, wherein the outer cover member includes a cylindrical body on which a needle slit is provided, through which a needle of the needle body passes and which covers the needle, wherein the inner cover member includes a shield plate capable of being moved along an inner face of the cylindrical body between an opening position at which the needle slit is opened and a closing position at which the needle slit is closed, and wherein in a process of covering the needle with the protector main body, the shield plate moves from the opening position to the closing position in an interlocking relationship with movement of the needle body, so as to close the needle slit as the needle is inserted into the needle slit.

2. The protector according to claim 1, wherein the outer cover member comprises:

an outer bottom for closing a proximal end side of the cylindrical body, and a cutaway portion provided on the outer bottom and into which the needle body is inserted;

the inner cover member comprises an inner wall disposed on the proximal end side of the shield plate; and the inner wall comprises:

a needle receiving edge portion which comes into contact with the needle body when the needle body is inserted into the cutaway portion, and a detachment preventing end portion for preventing detachment of the needle body.

3. The protector according to claim 2, wherein:

the needle receiving edge portion is disposed at a position displaced in a direction perpendicular to the direction in which the needle passes, with reference to a center axis of the inner cover member at the opening position, and crosses the cutaway portion, and the detachment preventing end portion is configured so as to close the cutaway portion when the detachment preventing end portion is at the closing position.

4. The protector according to claim 1, wherein:

the cylindrical body has a circumferential slit extending in a circumferential direction;

the inner cover member includes a projection for engagement with the circumferential slit; and the shield plate is configured so as to be movable from the closing position to the opening position, while the projection moves along the circumferential slit.

5. The protector according to claim 4, wherein:

the needle slit and the circumferential slit communicate with each other; and the shield plate is capable of moving the projection in an axial direction along the needle slit.

6. The protector according to claim 1, wherein:

the cylindrical body has a conical shape with a diameter that increases toward the distal end side; and when the shield plate moves from the closing position to the opening position, the needle body is positioned inside the outer cover member.

7. The protector according to claim 1, wherein the cylindrical body comprises a circular cylinder having a substantially fixed diameter, and is disposed at a position displaced in the direction in which the needle passes, with reference to a center axis of the inner cover member.

8. The protector according to claim 1, wherein at least one of the outer cover member and the inner cover member includes a lid member for closing the distal end thereof.

9. A protector assembly comprising:

a protector; and a needle body on which a supporting member of the protector is mounted, wherein the protector further comprises:

a supporting member mounted on a needle body, and a protector main body including an outer cover member disposed tiltably with respect to the supporting member, and an inner cover member disposed on the inner side of the outer cover member, the outer cover member comprises a cylindrical body on which a needle slit is provided, through which a needle of the needle body passes and which covers the needle, the inner cover member comprises a shield plate capable of being moved along an inner face of the cylindrical body, between an opening position at which the needle slit is opened and a closing position at which the needle slit is closed, and wherein in a process of covering the needle with the protector main body, the shield plate moves from the opening position to the closing position in an interlocking relationship with movement of the needle body, so as to close the needle slit as the needle is inserted into the needle slit.

10. The protector assembly according to claim 9, wherein the outer cover member comprises:

an outer bottom for closing a proximal end side of the cylindrical body, and a cutaway portion provided on the outer bottom and into which the needle body is inserted;

the inner cover member comprises an inner wall disposed on the proximal end side of the shield plate;

the inner wall comprises:

a needle receiving edge portion which comes into contact with the needle body when the needle body is inserted into the cutaway portion, and a detachment preventing end portion for preventing detachment of the needle body, wherein the needle receiving edge portion is disposed at a position displaced in a direction perpendicular to the direction in which the needle passes, with reference to a center axis of the inner cover member at the opening position.

11. The protector assembly according to claim 10, wherein the distance between the center of the needle slit and a center axis of the inner cover member is equal to or greater than one half the radius of the needle body, but is equal to or smaller than twice the radius of the needle body.

* * * * *